(12) United States Patent
Havel et al.

(10) Patent No.: US 8,998,929 B2
(45) Date of Patent: Apr. 7, 2015

(54) MEDICAL DEVICE SYSTEM AND APPARATUS FOR GUIDING THE PLACEMENT OF A SUBCUTANEOUS DEVICE

(75) Inventors: William J. Havel, Maple Grove, MN (US); Vladimir P. Nikolski, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 800 days.

(21) Appl. No.: 12/432,028

(22) Filed: Apr. 29, 2009

(65) Prior Publication Data

US 2010/0030229 A1 Feb. 4, 2010

Related U.S. Application Data

(60) Provisional application No. 61/190,052, filed on Jul. 31, 2008, provisional application No. 61/116,492, filed on Nov. 20, 2008.

(51) Int. Cl.
*A61B 19/00* (2006.01)
*A61B 17/34* (2006.01)
(Continued)

(52) U.S. Cl.
CPC ......... *A61B 17/3468* (2013.01); *A61B 17/3462* (2013.01); *A61B 17/3472* (2013.01); *A61B 2017/00026* (2013.01); *A61B 2017/0003* (2013.01); *A61B 2017/00561* (2013.01); *A61B 2017/306* (2013.01); *A61B 2017/320044* (2013.01); *A61B 2017/320056* (2013.01); *A61N 1/046* (2013.01); *A61N 1/0504* (2013.01)

(58) Field of Classification Search
USPC ............... 606/129, 159, 108, 1, 41, 201–204; 604/115–117, 508, 523; 607/115, 116, 607/117, 118, 119, 120, 149, 152, 122; 206/714–718; 220/280; 428/34.1, 35.7, 428/35.9, 40.1, 156
See application file for complete search history.

(56) References Cited

U.S. PATENT DOCUMENTS

| 3,515,129 A | 6/1970 | Truhan |
| 4,010,757 A | 3/1977 | Jula et al. |

(Continued)

FOREIGN PATENT DOCUMENTS

| DE | 19713266 A1 | 10/1998 |
| DE | 202006011664 U1 | 11/2006 |

(Continued)

OTHER PUBLICATIONS (PCT US2009/050188) PCT Notification of Transmittal of the International Search Report and the Written Opinion of the International Searching Authority.

*Primary Examiner* — Katrina Stransky
(74) *Attorney, Agent, or Firm* — Michael C. Soldner

(57) ABSTRACT

A medical device system for advancing a subcutaneous device to a desired implant site that includes a strap extending along a length from a proximal end to a distal end, a first flange and a second flange extending along a portion of the length of the strap, a base portion extending along a portion of the length of the strap between the first flange and the second flange, and an indentation extending from the proximal end to the distal end of the strap, the indentation formed by the first flange, the second flange, and the base portion, wherein the first flange and the second flange include curved bottom portions that make contact with and compress a tissue layer to position the tissue layer within the indentation during the placement of the subcutaneous device.

12 Claims, 19 Drawing Sheets

(51) Int. Cl.
  *A61N 1/04* (2006.01)
  *A61B 17/00* (2006.01)
  *A61B 17/30* (2006.01)
  *A61B 17/32* (2006.01)
  *A61N 1/05* (2006.01)

(56) References Cited

U.S. PATENT DOCUMENTS

| | | | | |
|---|---|---|---|---|
| 4,314,568 A * | 2/1982 | Loving | | 606/201 |
| 4,316,461 A * | 2/1982 | Marais et al. | | 604/179 |
| 4,424,818 A | 1/1984 | Doring et al. | | |
| 4,832,687 A | 5/1989 | Smith, III | | |
| 4,844,258 A | 7/1989 | Boeckmann et al. | | |
| 4,865,590 A * | 9/1989 | Marmar | | 604/180 |
| 4,958,053 A * | 9/1990 | Boeckmann et al. | | 206/714 |
| 5,064,064 A * | 11/1991 | Itou et al. | | 206/714 |
| 5,112,313 A * | 5/1992 | Sallee | | 604/180 |
| 5,269,803 A * | 12/1993 | Geary et al. | | 606/201 |
| 5,300,106 A | 4/1994 | Dahl et al. | | |
| 5,415,647 A * | 5/1995 | Pisarik | | 604/115 |
| 5,437,640 A | 8/1995 | Schwab | | 604/116 |
| 5,498,233 A * | 3/1996 | Stojanovic | | 602/19 |
| 5,693,032 A * | 12/1997 | Bierman | | 604/180 |
| 5,759,150 A * | 6/1998 | Konou et al. | | 600/114 |
| 5,782,841 A | 7/1998 | Ritz et al. | | |
| 5,865,827 A * | 2/1999 | Bullister | | 606/1 |
| 5,911,707 A * | 6/1999 | Wolvek et al. | | 604/116 |
| 5,944,732 A | 8/1999 | Raulerson et al. | | |
| 6,080,102 A * | 6/2000 | Konou et al. | | 600/114 |
| 6,324,414 B1 | 11/2001 | Gibbons et al. | | |
| 6,360,750 B1 | 3/2002 | Gerber et al. | | |
| 6,605,094 B1 | 8/2003 | Mann et al. | | |
| 6,671,554 B2 | 12/2003 | Gibson et al. | | |
| 7,025,760 B2 | 4/2006 | Miller et al. | | |
| 7,092,765 B2 | 8/2006 | Geske et al. | | |
| 7,186,214 B2 | 3/2007 | Ness | | |
| 7,218,970 B2 | 5/2007 | Ley et al. | | |
| 7,299,092 B2 * | 11/2007 | Bardy et al. | | 607/5 |
| 2004/0059348 A1 * | 3/2004 | Geske et al. | | 606/129 |
| 2004/0204728 A1 | 10/2004 | Haefner | | |
| 2004/0204734 A1 | 10/2004 | Wagner et al. | | |
| 2004/0204735 A1 | 10/2004 | Shiroff et al. | | |
| 2004/0260370 A1 | 12/2004 | Ley et al. | | |
| 2005/0090852 A1 * | 4/2005 | Layne et al. | | 606/190 |
| 2005/0137668 A1 * | 6/2005 | Khan | | 607/118 |
| 2006/0122676 A1 | 6/2006 | Ko et al. | | |
| 2006/0173474 A1 | 8/2006 | Wellman et al. | | |
| 2007/0060832 A1 | 3/2007 | Levin | | |
| 2007/0135847 A1 | 6/2007 | Kenknight | | |
| 2007/0185527 A1 * | 8/2007 | Babaev | | 606/204 |
| 2007/0191920 A1 | 8/2007 | Ley et al. | | |
| 2008/0200925 A1 * | 8/2008 | Johnson et al. | | 606/129 |
| 2008/0269763 A1 | 10/2008 | Bonde et al. | | |

FOREIGN PATENT DOCUMENTS

| | | |
|---|---|---|
| GB | 1078187 A | 8/1967 |
| WO | 9956633 A | 11/1999 |
| WO | 03018110 A2 | 3/2003 |
| WO | 2004026393 A2 | 4/2004 |
| WO | 2004089780 A | 10/2004 |
| WO | 2007005297 A | 1/2007 |
| WO | 2007060972 A | 5/2007 |

* cited by examiner

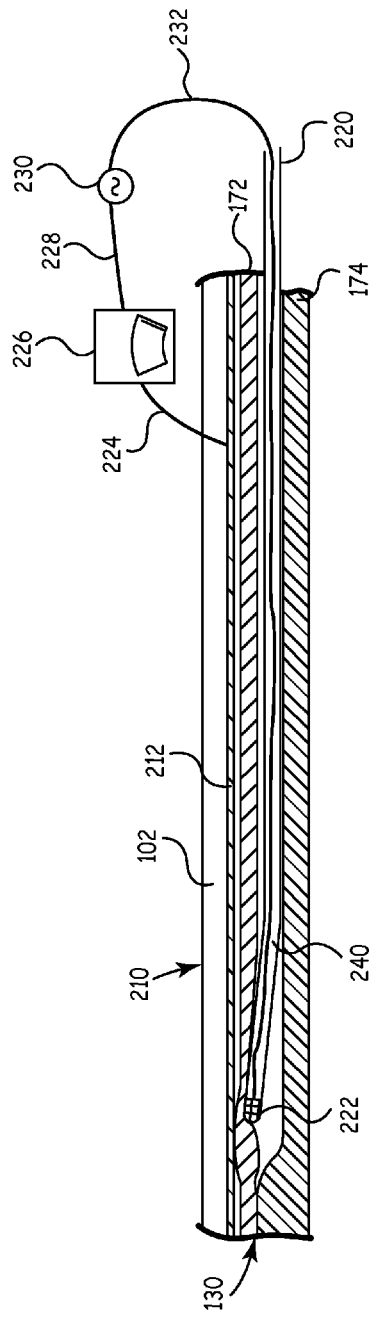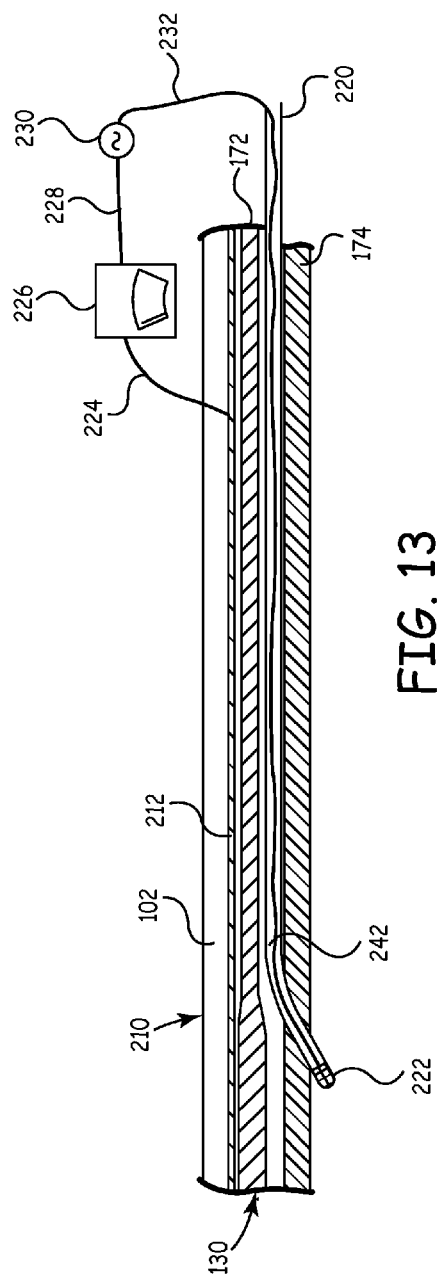
FIG. 12
FIG. 13

MEDICAL DEVICE SYSTEM AND APPARATUS FOR GUIDING THE PLACEMENT OF A SUBCUTANEOUS DEVICE

RELATED APPLICATION

This application claims the benefit of and priority to U.S. Provisional Application Ser. No. 61/116,492, filed Nov. 20, 2008, entitled, "Apparatus for Guiding The Placement of a Subcutaneous Device", and to U.S. Provisional Application Ser. No. 61/190,052, filed Jul. 31, 2008, entitled, "Apparatus for Guiding The Placement of a Subcutaneous Device" the contents of which are incorporated by reference herein in its entirety.

CROSS-REFERENCE TO RELATED APPLICATIONS

Cross-reference is hereby made to the commonly assigned related U.S. patent application Ser. No. 12/432,014 filed Apr. 29, 2009, now abandoned, entitled "MEDICAL DEVICE SYSTEM AND APPARATUS FOR GUIDING THE PLACEMENT OF A SUBCUTANEOUS DEVICE", to Havel et al.; and U.S. patent application Ser. No. 12/432,052 filed Apr. 29, 2009, now abandoned, entitled "MEDICAL DEVICE SYSTEM AND APPARATUS FOR GUIDING THE PLACEMENT OF A SUBCUTANEOUS DEVICE", to Havel et al., and U.S. patent application Ser. No. 12/431,926 filed Apr. 29, 2009, entitled "APPARATUS FOR GUIDING THE PLACEMENT OF A SUBCUTANEOUS DEVICE" to Havel et al.; filed concurrently herewith and incorporated herein by reference in their entireties.

FIELD OF THE INVENTION

The present disclosure relates to subcutaneous medical devices, and in particular, to an apparatus and medical device system for subcutaneously advancing a subcutaneous device to a desired implant site during an implantation procedure.

BACKGROUND OF THE INVENTION

A subcutaneous device, such as a coil electrode for an implantable cardioverter-defibrillator (ICD) positioned along a lead body, is typically implanted in a patient while the patient is lying supine on his or her back. The subcutaneous device is implanted using a tunneling tool that provides enough stiffness and pushability to create a space between the subcutaneous and muscular plane. However, since the patient is typically positioned on his or her back, it is difficult for a physician to maneuver a tunneling tool around the curvature of the posterior axilla to continue tunneling from the axilla to the spine.

One potential problem that a physician may encounter while implanting a subcutaneous device using a tunneling tool relates to the tendency of the tunneling tool to turn inward, between the ribs and into muscle of the patient, potentially creating a pneumothorax. In addition, the tunneling tool may also have a tendency to turn outward, potentially puncturing the skin. In order to prevent the tunneling from turning outward, a non-sterile scrub nurse places a hand under the patient's back to help guide the tunneling tool and to give the skin support so that the tunneling tool does not penetrate the skin. In addition, x-ray or other suitable imaging systems may need to be utilized to help guide the tunneling tool to the desire location.

Therefore, a need exists for an improved apparatus to subcutaneously tunnel a device to a desired implant site during an implantation procedure.

BRIEF DESCRIPTION OF THE DRAWINGS

FIG. 12 illustrates a cross-sectional view of another embodiment of using the tunneling tool and the apparatus for guiding the placement of a subcutaneous device in a patient.

FIG. 13 illustrates a cross-sectional view of another embodiment of using the tunneling tool and the apparatus for guiding the placement of a subcutaneous device in a patient.

DETAILED DESCRIPTION OF THE INVENTION

Figure 1A:
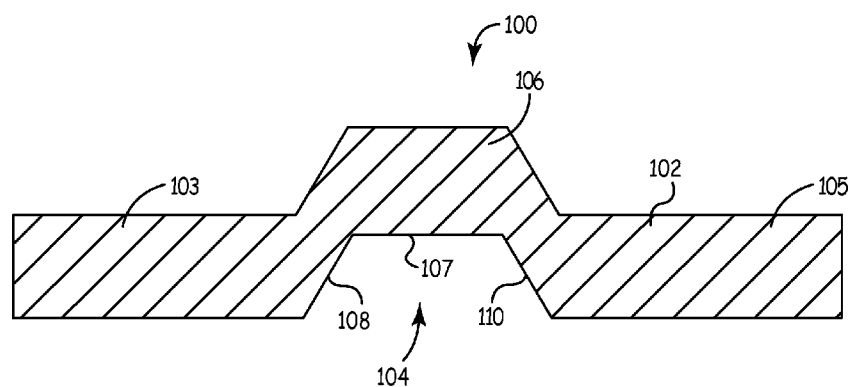
FIG. 1A illustrates a cross-sectional view of one embodiment of an apparatus for guiding the placement of a subcutaneous device.
Figure 1B:
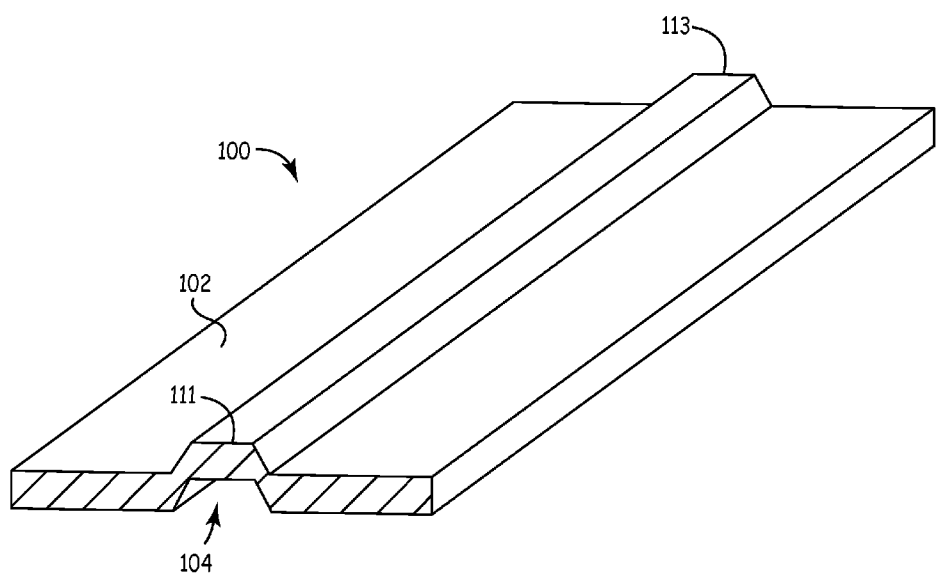
FIG. 1B illustrates a perspective view of one embodiment of an apparatus for guiding the placement of a subcutaneous device.

FIG. 1A illustrates a cross-sectional view of one embodiment of an apparatus 100 for guiding the placement of a subcutaneous device. FIG. 1B illustrates a perspective view of apparatus 100. Apparatus 100 includes a strap 102 having a first flange 103, a second flange 105, and a base portion 106 positioned between the first flange 103 and the second flange 105. An indentation 104 extends along the length of strap 102, from a proximal end 111 to a distal end 113 of the strap 102, and is formed by a first sidewall portion 108 of the first flange 103, a second sidewall portion 110 of the second flange 105 positioned opposite the first sidewall portion 108, and a bottom wall 107 of the base portion 106 that extends between the first sidewall portion 108 and the second sidewall portion 110.

Apparatus 100 is positioned over the appropriate intercostal space from the mid-axilliary line to the spine of a patient. Apparatus 100 is then attached to the patient. Indentation 104 allows a fold of skin and fat layer of the patient to compress into indentation 104 or to be positioned within indentation 104 when the patient lies down on an operating table. Indentation 104 provides a mechanical guide for a tunneling tool during the placement of a subcutaneous device, such as a coil electrode or lead. Indentation 104 also provides for more precise placement of the subcutaneous device compared to typical methods. In addition, apparatus 100 holds the skin taut so that the skin does not fold or snag during tunneling. Apparatus 100 replaces the need to have a hand over the top of the patient's skin or the need to use x-ray or other imaging systems to assist the physician in guiding the tunneling tool.

Strap 102 is made of a semi-stiff material such that strap 102 conforms to a patient's body yet is sufficiently rigid to enable a fold of skin and fat layer of the patient to be compressed into indentation 104 with strap 102 attached to the patient. In one embodiment, strap 102 is made of plastic that has sufficient flex to conform to a patient's body. In another embodiment, strap 102 is made of rubber. In other embodiments, strap 102 is made of other suitable materials or combinations of materials. In one embodiment, strap 102 is approximately 12 to 18 inches long. In one embodiment, strap 102 can be sterilized.

Figure 2:
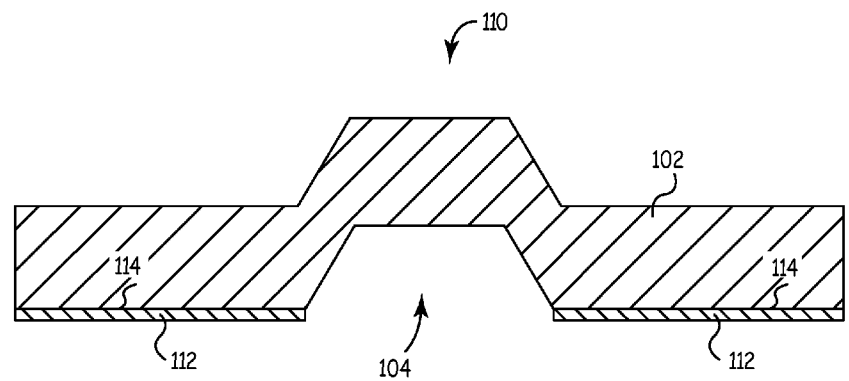
FIG. 2 illustrates a cross-sectional view of another embodiment of an apparatus for guiding the placement of a subcutaneous device.

FIG. 2 illustrates a cross-sectional view of another embodiment of an apparatus 110 for guiding the placement of a subcutaneous device. Apparatus 110 is similar to apparatus 100 previously described and illustrated with reference to FIGS. 1A and 1B, except that apparatus 110 includes adhesive 112. Adhesive 112 is attached to the bottom 114 of strap 102 adjacent to indentation 104. Adhesive 112 is used to attach strap 102 to a patient. In one embodiment, adhesive 112 includes a double sided tape. In other embodiments, adhesive 112 is applied to strap 102, which is then attached to a patient.

Figure 3:
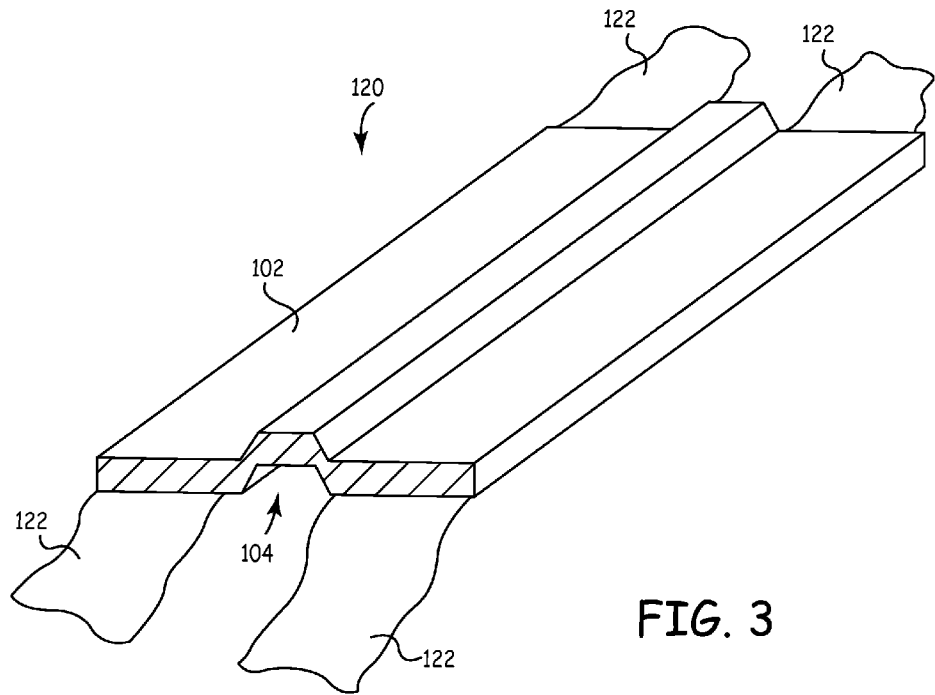
FIG. 3 illustrates a perspective view of another embodiment of an apparatus for guiding the placement of a subcutaneous device.

FIG. 3 illustrates a perspective view of another embodiment of an apparatus 120 for guiding the placement of a subcutaneous device. Apparatus 120 is similar to apparatus 100 previously described and illustrated with reference to FIGS. 1A and 1B, except that apparatus 120 includes bands 122. Bands 122 are attached to strap 102 adjacent to indentation 104. Bands 122 are used to attach strap 102 to a patient by wrapping bands 122 around the patient. In one embodiment, bands 122 are elasticized bands or other bands suitable for attaching strap 102 to a patient.

Figure 4:
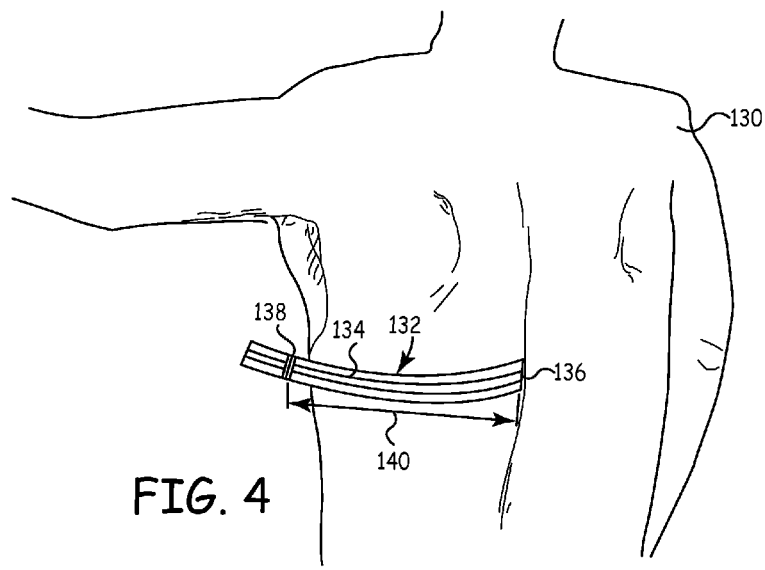
FIG. 4 is a diagram illustrating one embodiment of an apparatus attached to a patient for guiding the placement of a subcutaneous device.

FIG. 4 is a diagram illustrating one embodiment of an apparatus 132 attached to a patient 130 for guiding the placement of a subcutaneous device. Apparatus 132 includes a strap 134 including an indentation similar to apparatus 100 previously described and illustrated with reference to FIGS. 1A and 1B, apparatus 110 previously described and illustrated with reference to FIG. 2, or apparatus 120 previously described and illustrated with reference to FIG. 3.

In one embodiment, strap 134 is attached to patient 130 such that end 136 of strap 134 is at the desired location for the placement of a subcutaneous device. In one embodiment, strap 134 includes a mark or marks 138 for indicating how far a tunneling tool should be inserted to reach the desired location for the placement of a subcutaneous device at end 136 of strap 134. The distance between end 136 of strap 134 and mark or marks 138 is indicated at 140.

Figure 5:
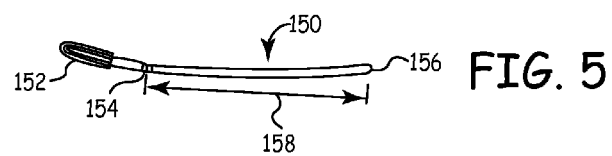
FIG. 5 is a diagram illustrating one embodiment of a tunneling tool.

FIG. 5 is a diagram illustrating one embodiment of a tunneling tool 150. Tunneling tool 150 includes a handle 152 at a proximal end and a tip 156 at a distal end. In one embodiment, tunneling tool 150 includes a mark or marks 154 at the proximal end near handle 152. Mark or marks 154 correspond to mark or marks 138 on strap 134 previously described and illustrated with reference to FIG. 4. The distance between mark or marks 154 and tip 156 of tunneling tool 150 indicated at 158 equals the distance between mark or marks 138 and end 136 of strap 134 indicated at 140. Therefore, by aligning mark or marks 154 on tunneling tool 150 with mark or marks 138 on strap 134, tip 156 of tunneling tool 150 is positioned at end 136 of strap 134 for placing a subcutaneous device at the desired location.

Figure 6A:
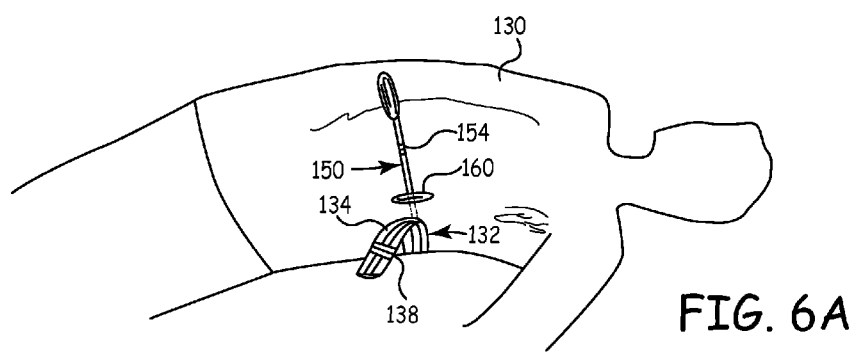
FIG. 6A is a diagram illustrating one embodiment of using the tunneling tool and the apparatus for guiding the placement of a subcutaneous device in a patient.

FIG. 6A is a diagram illustrating one embodiment of using tunneling tool 150 and apparatus 132 for guiding the placement of a subcutaneous device in a patient 130. Apparatus 132 is attached to patient 130 and the patient lies down on an operating table. A physician makes a subcutaneous pocket incision at 160 and inserts tunneling tool 150 into incision 160. As the physician advances tunneling tool 150 using apparatus 132 as a mechanical guide for the tunneling tool, the tunneling tool creates a space between the subcutaneous and muscular plane in patient 130. The physician continues to advance tunneling tool 150 until mark or marks 154 on tunneling tool 150 are aligned with mark or marks 138 on strap 134 indicating that tip 156 of tunneling tool 150 is at the desired location for placing the subcutaneous device.

Figure 6B:
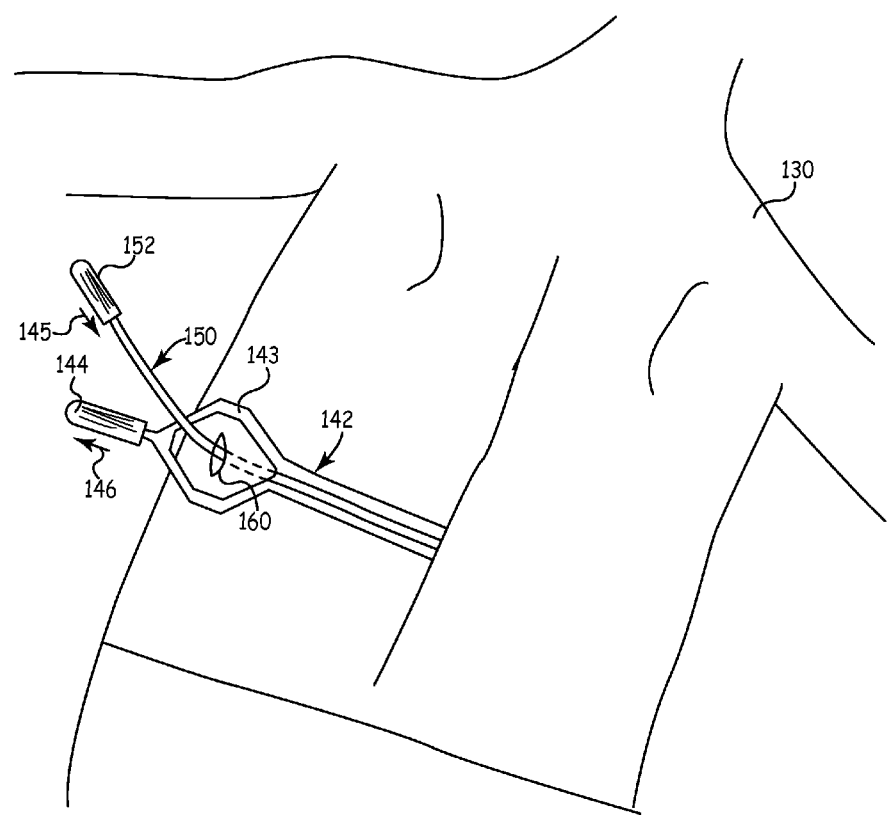
FIG. 6B is a diagram illustrating another embodiment of using the tunneling tool and an apparatus for guiding the placement of a subcutaneous device in a patient.

FIG. 6B is a diagram illustrating another embodiment of using tunneling tool 150 and an apparatus 142 for guiding the placement of a subcutaneous device in a patient 130. In this embodiment, apparatus 142 includes a handle 144, which is attached to the proximal end of the strap via an open frame connection 143. The open frame connection 143 between handle 144 and the strap provides a window through which a physician can access incision 160 and insert tunneling tool 150. As the physician inserts tunneling tool 150 by applying a force on handle 152 as indicated by arrow 145, a counterforce as indicated by arrow 146 is applied to handle 144 such that apparatus 142 keeps the skin of patient 130 taut to make advancement of tunneling tool 150 easier.

Figure 6C:
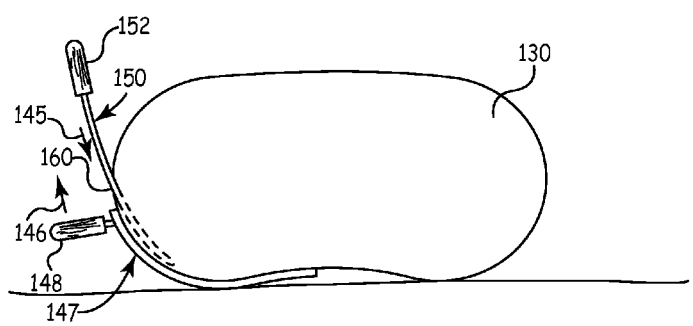
FIG. 6C is a diagram illustrating another embodiment of using the tunneling tool and an apparatus for guiding the placement of a subcutaneous device in a patient.

FIG. 6C is a diagram illustrating another embodiment of using tunneling tool 150 and an apparatus 147 for guiding the placement of a subcutaneous device in a patient 130. In this embodiment, apparatus 147 includes a handle 148, which is directly attached to the proximal end of the strap. In one embodiment, handle 148 is attached to the strap at a 90 degree angle or another suitable angle such that handle 148 does not interfere with handle 152 of tunneling tool 150. As the physician inserts tunneling tool 150 by applying a force on handle 152 as indicated by arrow 145, a counterforce as indicated by arrow 146 is applied to handle 148 such that apparatus 147 keeps the skin of patient 130 taut to make advancement of tunneling tool 150 easier.

Figure 7:
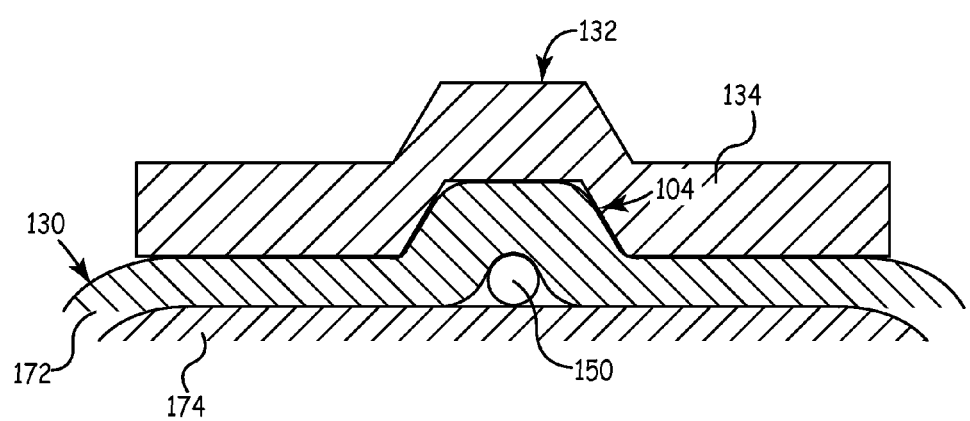
FIG. 7 illustrates a cross-sectional view of one embodiment of using the tunneling tool and the apparatus for guiding the placement of a subcutaneous device in a patient.

FIG. 7 illustrates a cross-sectional view of one embodiment of using tunneling tool 150 and apparatus 132 for guiding the placement of a subcutaneous device in a patient 130. A skin and fat layer or cutaneous tissue 172 of patient 130 is compressed into indentation 104 of strap 134. By using strap 134 as a mechanical guide, tunneling tool 150 creates a space between the skin and fat layer 172 and muscle 174.

Figure 8:
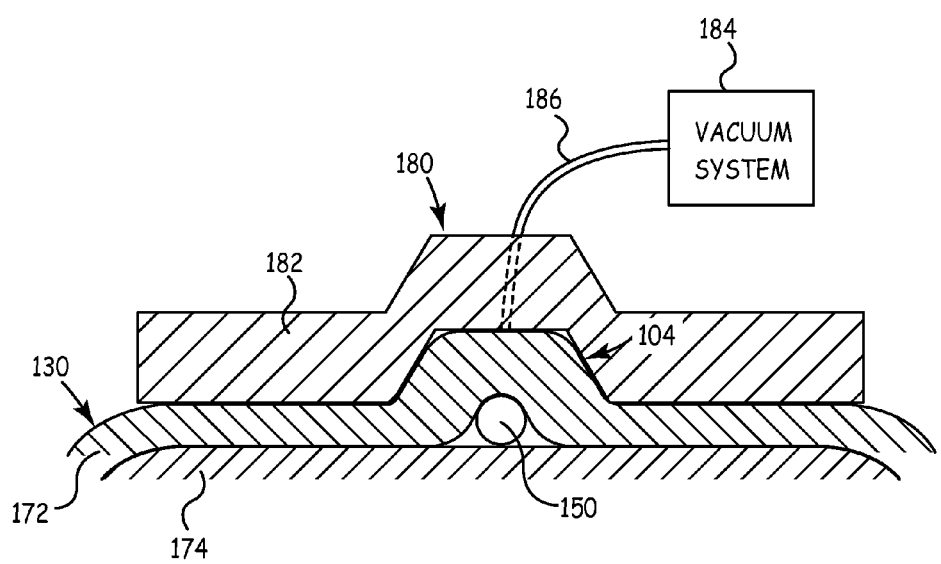
FIG. 8 illustrates a cross-sectional view of another embodiment of using the tunneling tool and an apparatus including a vacuum system for guiding the placement of a subcutaneous device in a patient.

FIG. 8 illustrates a cross-sectional view of another embodiment of using tunneling tool 150 and an apparatus 180 including a vacuum system 184 for guiding the placement of a subcutaneous device in a patient 130. A vacuum system 184 is attached to apparatus 180 through a vacuum line 186. Vacuum line 186 passes through strap 182 to indentation 104. The vacuum pulls the skin upward to be positioned within indentation 104 and holds skin and fat layer 172 in indentation 104. In one embodiment, the vacuum is provided within indentation 104 along the entire length of strap 182 using a network of vacuum lines within strap 182. In one embodiment, the ends of strap 182 are sealed to prevent air outside of strap 182 from entering vacuum system 184.

Figure 9:
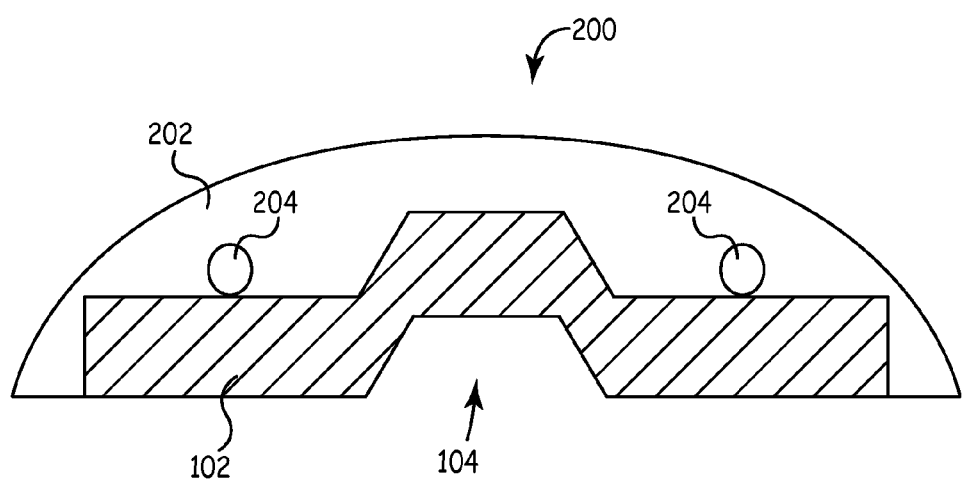
FIG. 9 illustrates a cross-sectional view of another embodiment of an apparatus for guiding the placement of a subcutaneous device.

FIG. 9 illustrates a cross-sectional view of another embodiment of an apparatus 200 for guiding the placement of a subcutaneous device. Apparatus 200 is similar to apparatus 100 previously described and illustrated with reference to FIGS. 1A and 1B, except that apparatus 200 includes additional material 202. In one embodiment, the top and sidewalls of strap 102 are coated with a polymer 202 or other suitable material. Material 202 is selected such that apparatus 200 is smooth to the touch and is slippery to allow a patient to move on an operating table without binding or sticking to the table surface.

In one embodiment, a hollow channel or channels 204 are provided along the length of strap 102 through material 202. In another embodiment, channels 204 are provided through strap 102. After apparatus 200 is attached to a patient, a tunneling tool can be inserted into a channel 204 to shape the tunneling tool to conform to the patient's body prior to inserting the tunneling tool into the patient's body.

Figure 10:
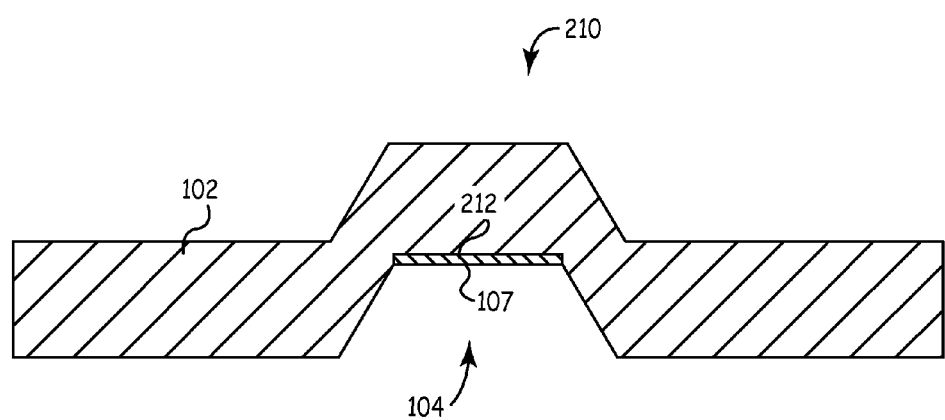
FIG. 10 illustrates a cross-sectional view of another embodiment of an apparatus for guiding the placement of a subcutaneous device.

FIG. 10 illustrates a cross-sectional view of another embodiment of an apparatus 210 for guiding the placement of a subcutaneous device. Apparatus 210 is similar to apparatus 100 previously described and illustrated with reference to FIGS. 1A and 1B, except that apparatus 210 includes a conductive surface 212 along the base portion 106 of indentation 104. Conductive surface 212 provides an indifferent conductor or electrode for an impedance measurement between electrode 212 and the tip of a lead or the tip of a tunneling tool, which provides the active probe for the impedance measurement. In one embodiment, the impedance measurement provides an electrical guide for guiding the tunneling tool during placement of a subcutaneous device. The impedance measurement provides an indication of the depth of the tunneling tool beneath the skin. As the tunneling tool moves toward a patient's skin, the impedance decreases. As the tunneling move toward a patient's muscle, the impedance increases.

Figure 11:
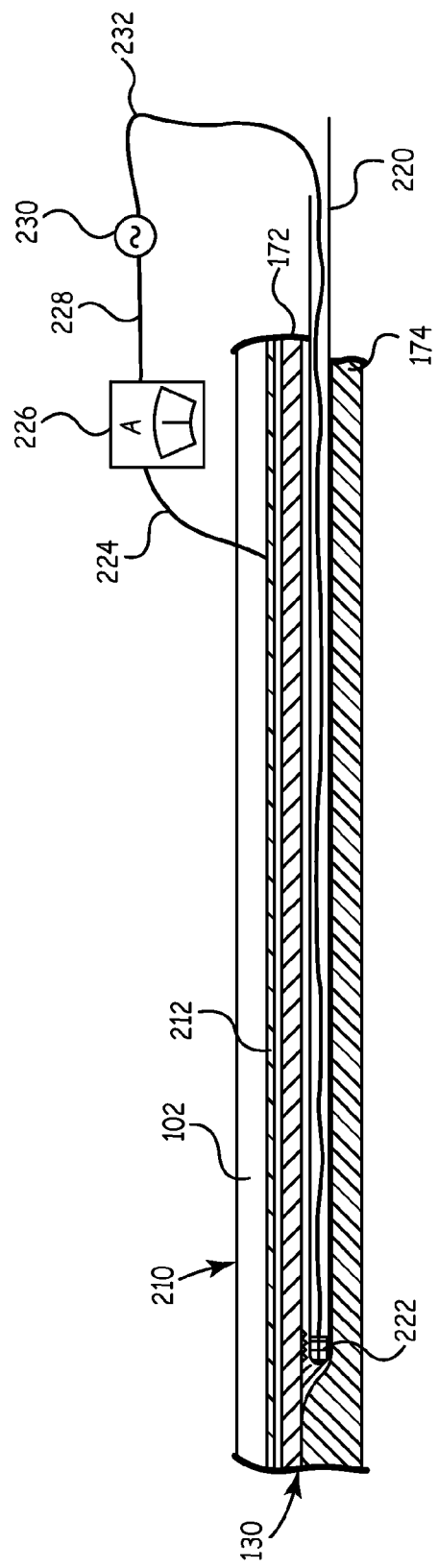
FIG. 11 illustrates a cross-sectional view of another embodiment of using the tunneling tool and the apparatus for guiding the placement of a subcutaneous device in a patient.

FIG. 11 illustrates a cross-sectional view of another embodiment of using a tunneling tool 220 and apparatus 210 for guiding the placement of a subcutaneous device in a patient 130. Apparatus 210 including electrode 212 is attached to a patient 130. In one embodiment, a conductive gel or other suitable material is applied to electrode 212 before attaching apparatus 210 to the patient. Electrode 212 is electrically coupled to one side of an ammeter 226 through signal path 224. The other side of ammeter 226 is electrically coupled to one side of a voltage source 230 through signal path 228. The other side of voltage source 230 is electrically coupled to a tunneling tool electrode 222 through signal path 232. In one embodiment, tunneling tool electrode 222 is the tip of a lead. In another embodiment, tunneling tool electrode 222 is the tip of tunneling tool 220. Signal path 232 passes through the inside of tunneling tool 220 to the tunneling tool electrode 222. Except for the tunneling tool electrode 222, tunneling tool 220 is electrically insulated.

Voltage source 230 provides a voltage between electrode 212 and tunneling tool electrode 222. Ammeter 226 measures the current between electrode 212 and tunneling tool electrode 222. As the impedance between electrode 212 and tunneling tool electrode 222 increases, the current indicated by ammeter 226 between electrode 212 and tunneling tool electrode 222 decreases. As the impedance between electrode 212 and tunneling tool electrode 222 decreases, the current indicated by ammeter 226 between electrode 212 and tunneling tool electrode 222 increases. Therefore, by monitoring the current indicated by ammeter 226, the depth of tunneling tool 220 beneath the patient's skin can be determined. In this embodiment, tunneling tool 220 is in the desired space between cutaneous tissue 172 and muscle 174. As such, the needle of ammeter 226 is centered indicating that tunneling tool 220 is in the desired space. In other embodiments, ammeter 226 is replaced with a digital meter or other suitable monitor for indicating the impedance between electrode 212 and tunneling tool electrode 222.

FIG. 12 illustrates a cross-sectional view of another embodiment of using tunneling tool 220 and apparatus 210 for guiding the placement of a subcutaneous device in a patient 130. In this embodiment, tunneling tool 220 includes a bend at 240 that is pushing tunneling tool electrode 222 into cutaneous tissue 172 toward the patient's skin. As such, the needle of ammeter 226 is to the right indicating a lower impedance since tunneling tool 220 is approaching the patient's skin. The indication of impedance provided by ammeter 226 can be used to correct the position of tunneling tool 220 before tunneling tool 220 punctures the patient's skin.

FIG. 13 illustrates a cross-sectional view of another embodiment of using tunneling tool 220 and apparatus 210 for guiding the placement of a subcutaneous device in a patient 130. In this embodiment, tunneling tool 220 includes a bend at 242 that is pushing tunneling tool electrode 222 into muscle 174. As such, the needle of ammeter 226 is to the left indicating a higher impedance since tunneling tool 220 is in the patient's muscle 174. The indication of impedance provided by ammeter 226 can be used to correct the position of tunneling tool 220 before tunneling tool 220 creates a pneumothorax.

Figure 14:
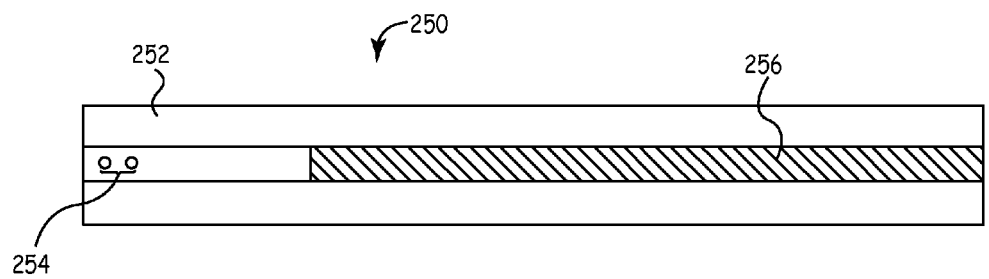
FIG. 14 illustrates a bottom view of another embodiment of an apparatus for guiding the placement of a subcutaneous device.

FIG. 14 illustrates a bottom view of another embodiment of an apparatus 250 for guiding the placement of a subcutaneous device. Apparatus 250 includes a strap 252 including a reference electrode 256 and a bipole electrode 254. Reference electrode 256 is similar to electrode 212 previously described and illustrated with reference to FIG. 10, except that reference electrode 256 does not extend the entire length of strap 252. Reference electrode 256 is used similarly to electrode 212. Bipole electrode 254 is used as a target for positioning the tip of a tunneling tool for the placement of a subcutaneous device.

Figure 15:
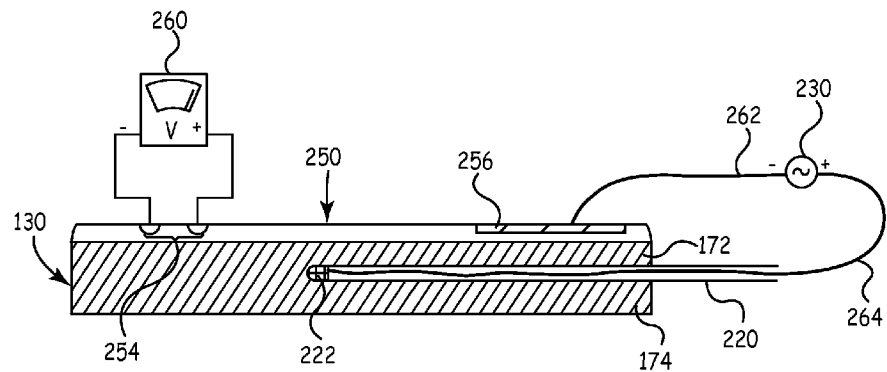
FIG. 15 illustrates a cross-sectional view of another embodiment of using the tunneling tool and the apparatus for guiding the placement of a subcutaneous device in a patient.

FIG. 15 illustrates a cross-sectional view of another embodiment of using tunneling tool 220 and apparatus 250 for guiding the placement of a subcutaneous device in a patient 130. Apparatus 250 including reference electrode 256 and bipole electrode 254 is attached to a patient 130. Apparatus 250 is attached to patient 130 such that bipole electrode 254 is positioned above the desired location for the placement of a subcutaneous device. Reference electrode 256 is electrically coupled to the negative terminal of voltage source 230 through signal path 262. The positive terminal of voltage source 230 is electrically coupled to tunneling tool electrode 222 through signal path 264. Bipole electrode 254 is electrically coupled to a voltmeter 260.

Voltage source 230 provide a voltage between reference electrode 256 and tunneling tool electrode 222. Bipole electrode 254 provides a target location for a subcutaneous device. Voltmeter 260 indicates the position of tunneling tool electrode 222 based on the polarity indicated by the needle of voltmeter 260. In this embodiment, tunneling tool 220 has not yet reached the target location. As such, the needle of voltmeter 260 is to the right indicating a positive polarity. Therefore, the physician should continue to advance tunneling tool 220 toward the target location.

Figure 16:
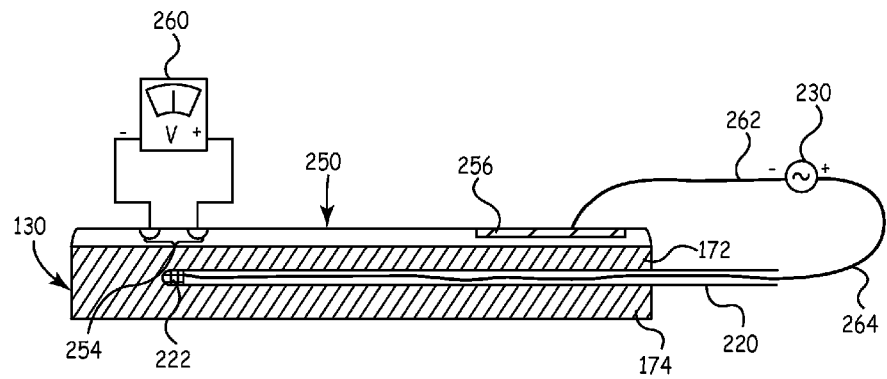
FIG. 16 illustrates a cross-sectional view of another embodiment of using the tunneling tool and the apparatus for guiding the placement of a subcutaneous device in a patient.

FIG. 16 illustrates a cross-sectional view of another embodiment of using tunneling tool 220 and apparatus 250 for guiding the placement of a subcutaneous device in a patient 130. In this embodiment, tunneling tool 220 has reached the target location. As such, the needle of voltmeter 260 is zeroed. Therefore, the physician should stop advancing tunneling tool 220 and place the subcutaneous device at the target location.

Figure 17:
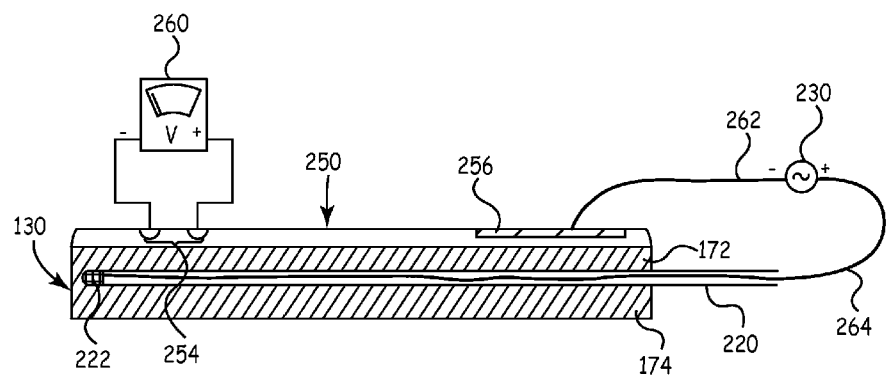
FIG. 17 illustrates a cross-sectional view of another embodiment of using the tunneling tool and the apparatus for guiding the placement of a subcutaneous device in a patient.

FIG. 17 illustrates a cross-sectional view of another embodiment of using tunneling tool 220 and apparatus 250 for guiding the placement of a subcutaneous device in a patient 130. In this embodiment, tunneling tool 220 has past the target location. As such, the needle of voltmeter 260 is to the left indicating a negative polarity. Therefore, the physician should stop advancing tunneling tool 220 and begin retreating tunneling tool 220 toward the target location.

Figure 18:
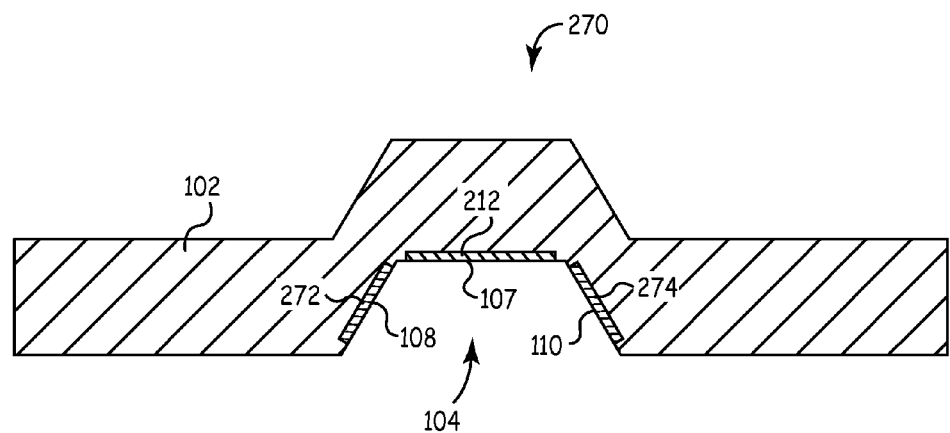
FIG. 18 illustrates a cross-sectional view of another embodiment of an apparatus for guiding the placement of a subcutaneous device.

FIG. 18 illustrates a cross-sectional view of another embodiment of an apparatus 270 for guiding the placement of a subcutaneous device. Apparatus 270 is similar to apparatus 210 previously described and illustrated with reference to FIG. 10, except that apparatus 270 includes a first conductive surface 272 along first sidewall portion 108 of indentation 104 and a second conductive surface 274 along second sidewall portion 110 of indentation 104. Conductive surface 272 provides a first indifferent conductor or first electrode for a first impedance measurement between first electrode 272 and the tip of a lead or the tip of a tunneling tool, which provides the active probe for the impedance measurement. Conductive surface 274 provides a second indifferent conductor or second electrode for a second impedance measurement between second electrode 274 and the tip of a lead or the tip of a tunneling tool.

In one embodiment, the first and second impedance measurements provide an electrical guide for assisting a physician in guiding the tunneling tool during placement of a subcutaneous device. The first and second impedance measurements provide an indication of the lateral position of the tunneling tool between first electrode 272 and second electrode 274. As the tunneling tool moves toward first electrode 272, the impedance between first electrode 272 and the tunneling tool decreases and the impedance between second electrode 274 and the tunneling tool increases. As the tunneling tool moves toward second electrode 274, the impedance between second electrode 274 and the tunneling tool decreases and the impedance between first electrode 272 and the tunneling tool increases.

Figure 19:
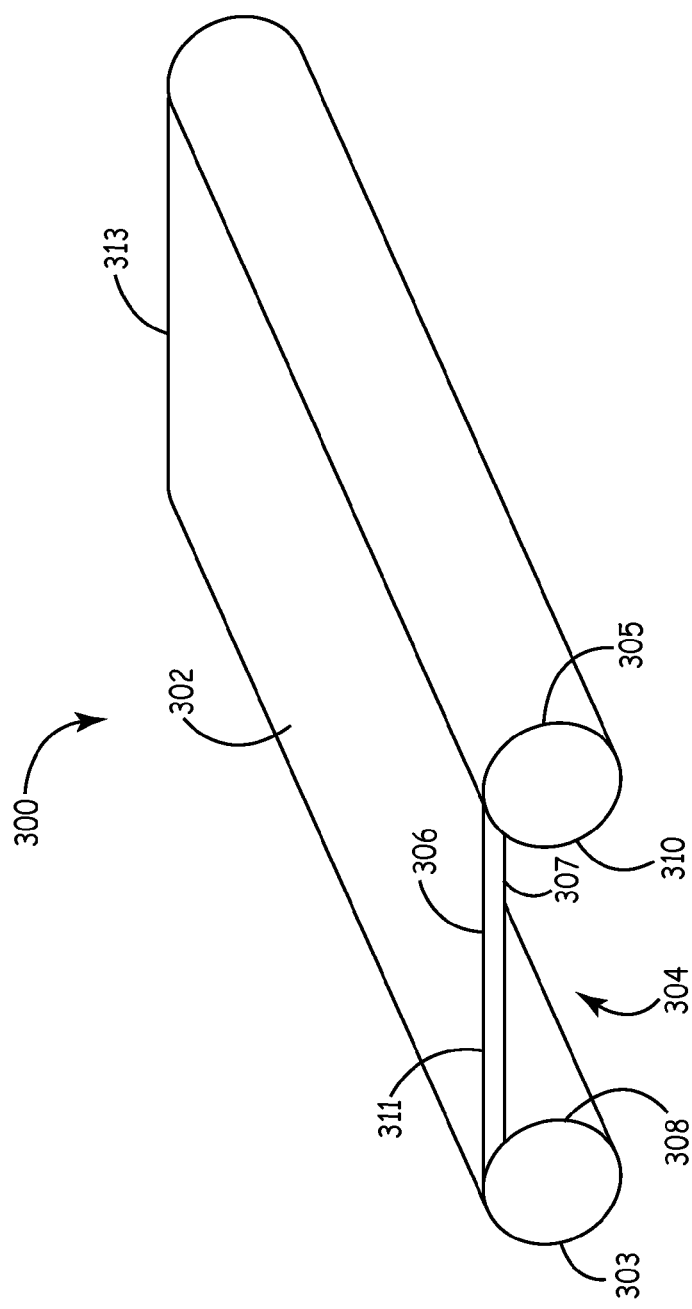
FIG. 19 is perspective view of an exemplary embodiment of an apparatus 300 for guiding the placement of a subcutaneous device.

FIG. 19 is perspective view of an exemplary embodiment of an apparatus 300 for guiding the placement of a subcutaneous device. Depending upon the physical attributes of the patient, such as torso size and shape, and the amount of fat that presents itself, there is sometimes a tendency for the tunneling tool 150 to advance out of the indentation 104 and slide under one of the first flange portion 103 and the second flange portion 105. As illustrated in FIG. 19, in order to reduce the tendency of the tunneling tool 150 to wander out of the indentation 104, apparatus 300 may include a strap 302 having a first curved flange 303, a second curved flange 305, and a base portion 306 extending between the first curved flange 303 and the second curved flange 305. An indentation 304 extends along the length of strap 302 from a proximal end 311 to a distal end 313 of the strap 302, and is formed by a first sidewall portion 308 of the first curved flange 303, a second sidewall portion 310 of the second curved flange 305 positioned opposite the first sidewall portion 308, and a bottom wall 307 of the base portion 306 that extends between the first sidewall portion 308 and the second sidewall portion 310. Sidewall portions 308 and 310 are curved in shape so as to extend within indentation 304.

Figure 20:
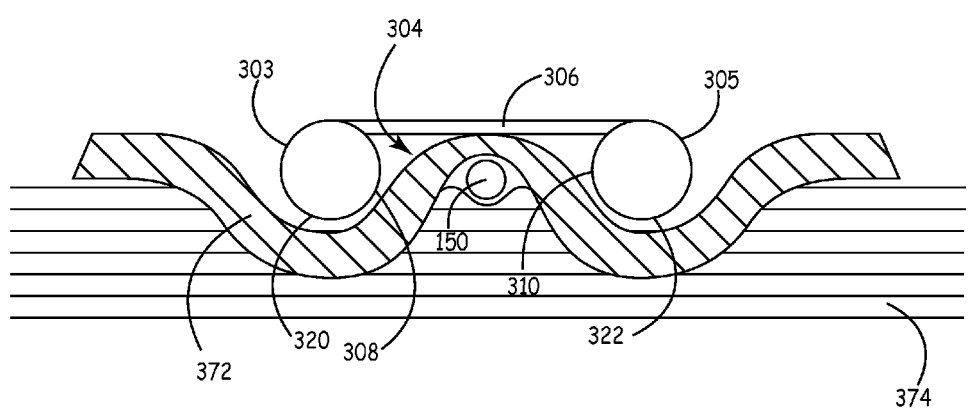
FIG. 20 is a cross-sectional view of one embodiment of using tunneling tool 150 and apparatus 300 for guiding the placement of a subcutaneous device in a patient 130.

FIG. 20 is a cross-sectional view of one embodiment of using tunneling tool 150 and apparatus 300 for guiding the placement of a subcutaneous device in a patient 130. As illustrated in FIGS. 19 and 20, the first curved flange 303 and the second curved flange 305 include curved bottom portions 320 and 322, respectively, that make contact with and compress the fat layer 372 and the muscle layer 374 of the patient, increasing the amount of the fat layer 372 and the muscle layer 374 that is positioned within the indentation 304 when the strap 302 is positioned on the patient. In addition, both the first sidewall portion 308 and the second sidewall portion 310 include curved portions that further compress the tissue as it becomes positioned within the indentation 304. In this way, the tendency of the tunneling tool 150 to wander out of the indentation 104 is reduced by the curved portions of the first curved flange 303 and the second curved flange 305.

Figure 21:
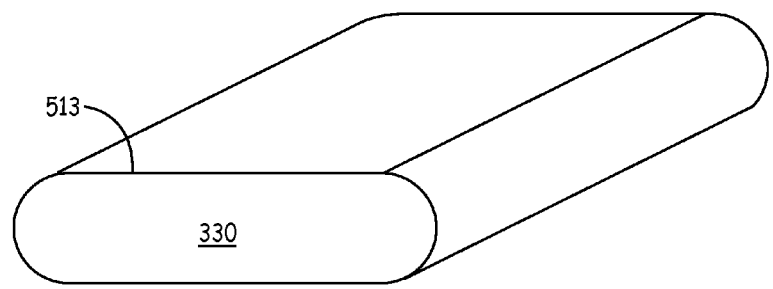
FIG. 21 is a planar view of a distal end of an apparatus for guiding the placement of a subcutaneous device in a patient.

FIG. 21 is a planar view of a distal end of an apparatus for guiding the placement of a subcutaneous device in a patient. As illustrated in FIG. 21, the distal end 513 of the strap 102 or 302 may include a distal end wall member 330 to block further advancement of the tunneling tool 150 beyond the distal end 313 of the strap 302, and as an indication to the clinician that the tunneling tool 150 is fully advanced.

Figure 22:
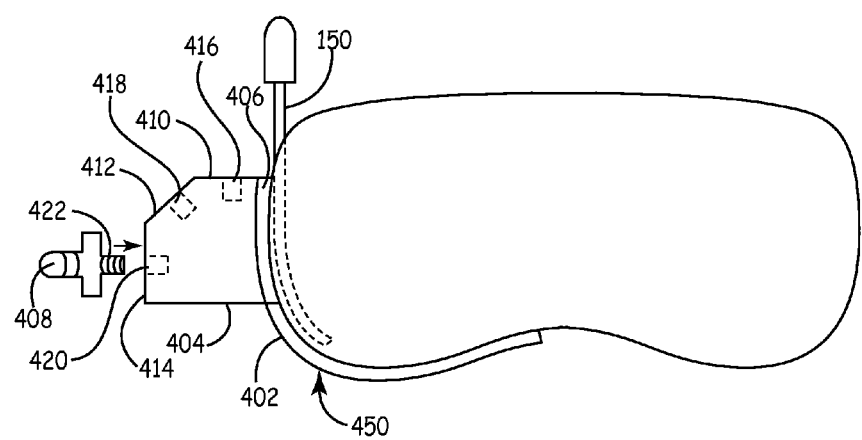
FIG. 22 is a diagram illustrating an embodiment of the use of a tunneling tool and an apparatus for guiding the placement of a subcutaneous device in a patient.

FIG. 22 is a diagram illustrating an embodiment of the use of a tunneling tool and an apparatus for guiding the placement of a subcutaneous device in a patient. As illustrated in FIG. 22, an apparatus for guiding the placement of a subcutaneous device may include a strap 402, similar to strap 302 of FIG.

19, having a handle orientation member 404, positioned at a proximal end 406 of strap 402. Handle orientation member 404 enables the user to selectively determine the desired orientation of a handle 408 of the strap 402. In particular, handle orientation member 404 includes a first side wall 410, a second side wall 412 and a side third wall 414. First side wall 410 includes a first side wall threaded port 416, second side wall 412 includes a second side wall threaded port 418, and third side wall 414 includes a third side wall threaded port 420. Threaded ports 416-420 are sized to receive a corresponding threaded screw member 422 positioned on a handle 408. The side walls 410-414 are orientated at predetermined relative angles to enable the handle 408 to be selectively positioned relative to the strap 402.

For example, if it is desired that the handle 408 be positioned perpendicular to the strap 402, the threaded screw member 422 of handle 408 is positioned within threaded port 420 of third side wall 414. If it is desired that the handle 408 be positioned parallel to the strap 402, the threaded screw member 422 of handle 408 is positioned within threaded port 416 of first side wall 410. If it is desired that the handle 408 be position at an angle other than perpendicular or parallel to the strap 402, the threaded screw member 422 of handle 408 is positioned within threaded port 418 of second side wall 412. In this way, the handle 408 may be detachably removed and positioned to be in any of the available orientations as desired.

Figure 23:
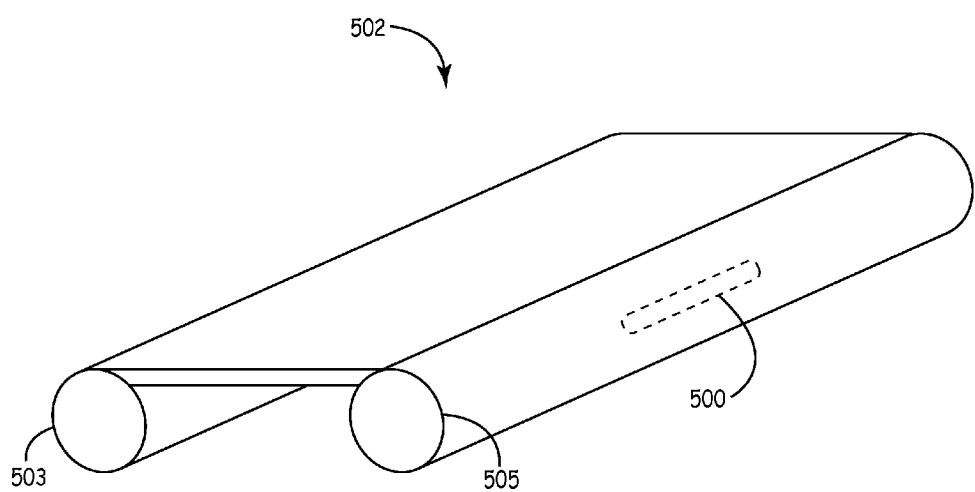
FIG. 23 is a perspective view of an exemplary embodiment of an apparatus for guiding placement of a subcutaneous device.

FIG. 23 is a perspective view of an exemplary embodiment of an apparatus for guiding placement of a subcutaneous device. Depending upon the physical attributes of the patient, such as torso size and shape, a radius of curvature formed by the strap 402 when positioned along the body of the patient may sometimes result in there being a location where the radius of curvature of the strap 402 may cause difficulties in advancing the tunneling tool within the strap 402. For example, the angle of curvature of the strap along a location 450 (FIG. 22) where the strap 402 is advanced around the patient's side to the spine, may result in navigation of the tunneling tool 150 through the strap 402 along the location 450 to become difficult.

The apparatus of FIG. 23 is a strap 502 similar to strap 302 of FIG. 19, for example, having a first curved flange 503 and a second curved flange 505. As illustrated in FIG. 23, the strap 502 may include one or more orientation members 500 positioned within one or both of the first curved flange 503 and the second curved flange 505 (only one orientation member is shown). Orientation members 500 may extend the full length of the curved flanges 503 and 505, or extend along only a predetermined portion of the one or more flanges 503 and 505, such as over a portion of the flanges 503 and 505 corresponding to the location 450 described above.

Figure 24:
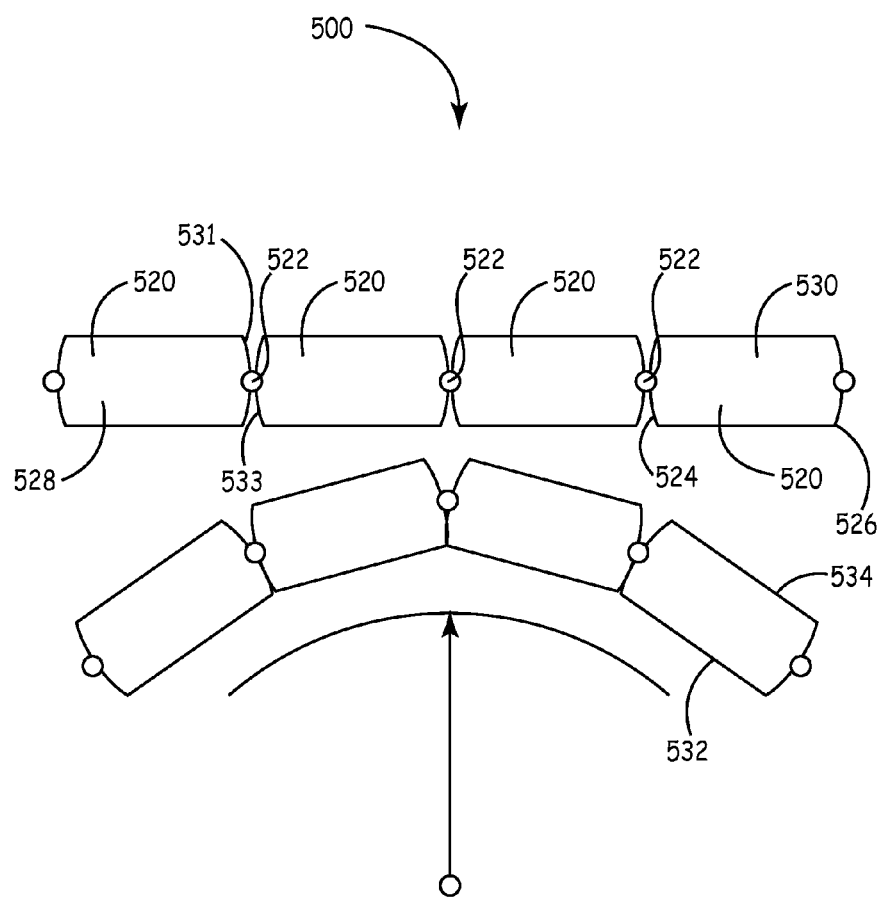
FIG. 24 is an illustration of an exemplary embodiment of the orientation member 500 of FIG. 23.

FIG. 24 is an illustration of an exemplary embodiment of the orientation member 500 of FIG. 23. As illustrated in FIG. 24, the orientation member 500 is formed having multiple segments 520 that are interconnected by hinge members 522. Each of the segments 520 extend from a first end 524 to a second end 526, so that the first end 524 of one of the segments 520 is spaced from the second end 526 of an adjacent one of the segments 520 by one of the hinge members 522. Only the second end 526 of a first segment 528 is spaced from the first end 524 of an adjacent segment 520, with the first end of segment 528 forming a first end of the orientation member 500, while only the first end of a last segment 530 is spaced from a second end 526 of an adjacent segment 520, with the second end 526 of the last segment 530 forming a second end of the orientation member 500.

Each of the first and second ends 524 and 526 are formed to have a first angled portion 531 extending at a predetermined angle between the hinge member 522 and a bottom side 532 of the segment 520, and a second angled portion 533 extending at a second predetermined angle between the hinge member 522 and a top side 534 of the segment 520. The first and second predetermined angles are chosen to limit the radius of curvature of the orientation member 500 to a value associated with the greatest radius of curvature that can be tolerated before making advancing of the tunneling tool 150 through the strap 502 difficult. In this way the orientation member 500 can be advanced between a first position in which adjacent first angled portions 531 are engaged, to a straight position in which the first and second angled portions 531 and 533 are all equally relatively spaced (shown in FIG. 24), to a second position in which adjacent second angled portions 533 are engaged against each other (shown). In this way, the orientation member 500 is positioned within the strap so that the orientation member 500 limits the radius of curvature of the strap 502 to help ensure ease of advancement of the tunneling tool within the strap 502. It is understood that the orientation member 500 may also be positioned within a base portion 506 of the strap 502, or within a combination of the base portion 506 and one or both of flanges 503 and 505 of the strap 502.

While the orientation member 500 is shown utilizing hinge members 522 to limit the orientation of the strap 502, it is understood that other designs may be utilized to limit the orientation of the strap 502, such the use of a material having a desire limited flexion corresponding to the desired limited radius of curvature. Furthermore, while the orientation member is describe being utilized in the strap having the curved flanges, the orientation member may also be utilized in the strap having the straight flanges described above and shown in FIGS. 1A and 1B.

Figure 25:
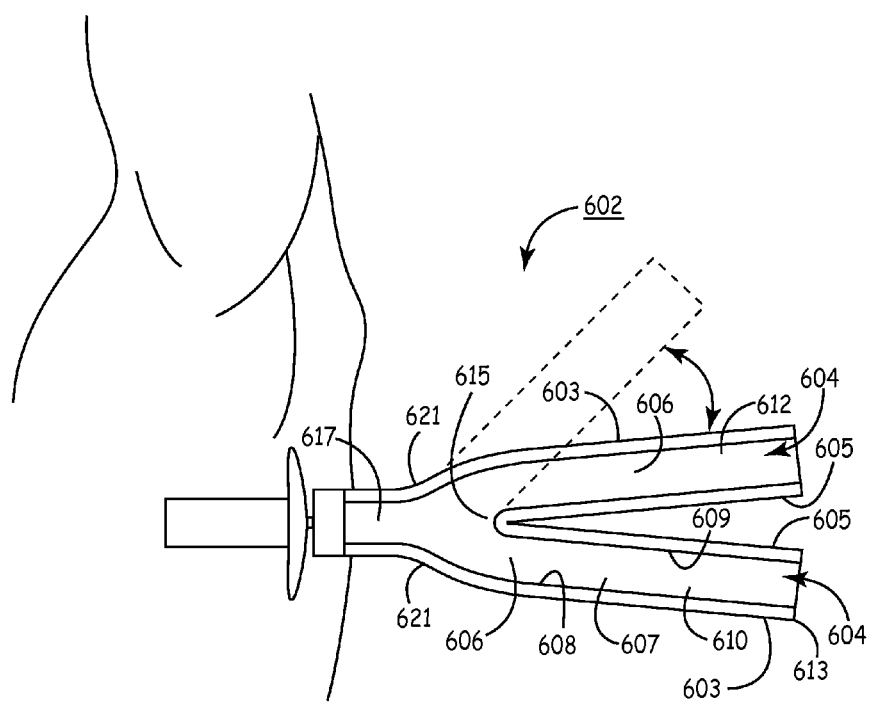
FIG. 25 is an illustration of an exemplary embodiment of an apparatus for guiding placement of a subcutaneous device in a patient.

FIG. 25 is an illustration of an exemplary embodiment of an apparatus for guiding placement of a subcutaneous device in a patient. As illustrated in FIG. 25, a strap 602 may be formed to have multiple pathways for advancing a tunneling tool to more than one location, so that multiple subcutaneous leads my be positioned at different locations within the patient. For example, the apparatus may include a first strap 610 and a second strap 612, each formed similar to the straps described above. For example, each are formed to include a first curved flange 603, a second curved flange 605, and a base portion 606 extending between the first curved flange 603 and the second curved flange 605. An indentation 604 extends along the length of strap 602 from a proximal end 617 to a distal end 613 of the strap 602, and is formed by a first sidewall portion 608 of the first curved flange 603, a second sidewall portion 609 of the second curved flange 605 positioned opposite the first sidewall portion 608, and a bottom wall 607 of the base portion 606 that extends between the first sidewall portion 608 and the second sidewall portion 609. The proximal ends 615 of the straps 610 and 612 form a common insertion path for the tunneling tool to be inserted within a proximal end 617 of the apparatus and extending along a desired one of the first and second straps 610 and 612.

One or more flexpoints 621 are formed along the straps 610 and 612, such as along proximal ends 615 of the straps 610 and 612 to allow for adjustment of a spacing angle between the two straps 610 and 612. In the alternative, a hinge member may be utilized to facilitate the variable separation of the two straps 610 and 612.

Embodiments provide an apparatus for assisting a physician in the placement of a subcutaneous device, such as a coil electrode for an implantable cardioverter-defibrillator (ICD) or other suitable subcutaneous device. The apparatus comprises a strap including an indentation for providing a mechanical guide for a tunneling tool. In addition, embodiments provide an electrical guide for assisting a physician in the placement of a subcutaneous device. The electrical guide is based on an impedance measurement or measurements between an electrode on a tunneling tool and an electrode or electrodes on the patient's skin. Embodiments also provide combinations of the mechanical guide and the electrical guide.

Although the present invention has been described with reference to preferred embodiments, workers skilled in the art will recognize that changes can be made in form and detail without departing from the spirit and scope of the present invention.

What is claimed is:

1. A medical device system for advancing a subcutaneous device to a desired implant site, the apparatus comprising:
    a strap having a major length extending from a proximal end to a distal end;
    a first flange comprising a first sidewall portion and a second flange comprising a second sidewall portion, the first flange and the second flange extending along the major length of the strap from the proximal end to the distal end;
    a base portion extending along the major length of the strap from the proximal end to the distal end, the base portion comprising a bottom wall extending from the first sidewall portion of the first flange to the second sidewall portion of the second flange; and
    an indentation extending from the proximal end to the distal end along the major length of the strap, the indentation formed by the first sidewall portion, the second sidewall portion, and the base portion, wherein the first flange and the second flange include bottom portions that make contact with and compress a tissue layer to position the tissue layer towards the base portion within the indentation as the subcutaneous device further advances the tissue layer to be positioned against one or more of the first sidewall portion, the second sidewall portion and the base portion of the indentation during the placement of the subcutaneous device; a tunneling tool having a tip to form a space between a first plane of tissue and a second plane of tissue as the tunneling tool is inserted into an incision in a patient's body; and a channel extending though the strap from the proximal end to the distal end along the major length of the strap; and wherein the strap is configured as a mechanical guide for guiding the placement of the tunneling tool as the tunneling tool is inserted along the indentation and into the space between the first plane of tissue and the second plane of tissue of the patient's body; and means for attaching the bottom portions to a patient's skin that comprises an adhesive.

2. The system of claim 1, wherein the second sidewall portion of the second flange is positioned opposite the first sidewall portion, wherein the first sidewall portion and the second sidewall portion have curved portions extending within the indentation.

3. The system of claim 1, further comprising:
    a conductive surface along the base portion of the indentation for measuring an impedance between the conductive surface and the tip of the tunneling tool to provide a depth of the tip of the tunneling tool beneath the first plane of tissue.

4. The system of claim 1, further comprising:
    a first conductive surface along the first flange for measuring a first impedance between the first conductive surface and the tip of the tunneling tool; and
    a second conductive surface along the second flange for measuring a second impedance between the second conductive surface and the tip of the tunneling tool, wherein the first impedance and the second impedance provide a lateral position of the tip of the tunneling tool between the first conductive surface and the second conductive surface.

5. The system of claim 1, further comprising:
    a first electrode positioned along the base portion;
    a second electrode positioned along the first flange;
    a third electrode positioned along the second flange; and
    a fourth electrode positioned along the tip of the tunneling tool, wherein a first impedance measurement between the first electrode and the fourth electrode provides a depth of the tip beneath the first plane of tissue, and wherein a second impedance measurement between the second electrode and the fourth electrode and a third impedance measurement between the third electrode and the fourth electrode provide a lateral position of the tip between the second electrode and the third electrode.

6. The system of claim 1, further comprising:
    a first mark positioned along the strap; and
    a second mark positioned along the tunneling tool, wherein the first mark is configured to be aligned with the second mark to indicate a location for placement of the tunneling tool.

7. The system of claim 1, wherein the strap comprises a bipole electrode configured to indicate a location for placement of the tunneling tool.

8. The system of claim 1, wherein the strap comprises a semi-stiff material such that the first flange and the second flange are conformable to a patient's body.

9. The system of claim 1, wherein the strap is adapted to be positioned along an intercostal space with the proximal end adjacent an incision site and the distal end adjacent a target location of a subcutaneous tool when it is advanced subcutaneously along the indentation.

10. A medical device system for advancing a subcutaneous device to a desired implant site, the apparatus comprising:
    a strap having a major length extending from a proximal end to a distal end;
    a first flange comprising a first sidewall portion and a second flange comprising a second sidewall portion, the first flange and the second flange extending along the major length of the strap from the proximal end to the distal end;
    a base portion extending along the major length of the strap from the proximal end to the distal end, the base portion comprising a bottom wall extending from the first sidewall portion of the first flange to the second sidewall portion of the second flange; and
    an indentation extending from the proximal end to the distal end along the major length of the strap, the indentation formed by the first sidewall portion, the second sidewall portion, and the base portion, wherein the first flange and the second flange include bottom portions that make contact with and compress a tissue layer to position the tissue layer towards the base portion within the indentation as the subcutaneous device further advances the tissue layer to be positioned against one or more of the first sidewall portion, the second sidewall portion and the base portion of the indentation during placement of the subcutaneous device; a tunneling tool having a tip to form a space between a first plane of tissue and a second plane of tissue as the tunneling tool is inserted into an incision in a patient's body; and a channel extending though the strap from the proximal end to the distal end along the major length of the strap; and wherein the strap is configured as a mechanical guide for guiding the placement of the tunneling tool as the tunneling tool is inserted along the indentation and into the space between the first plane of tissue and the second plane of tissue of the patient's body; and means for attaching the bottom portions to a patient's skin that comprises bands attached to the strap.

11. A medical device system for advancing a subcutaneous device to a desired implant site, the apparatus comprising:
   a strap having a major length extending from a proximal end to a distal end;
   a first flange comprising a first sidewall portion and a second flange comprising a second sidewall portion, the first flange and the second flange extending along the major length of the strap from the proximal end to the distal end;
   a base portion extending along the major length of the strap from the proximal end to the distal end, the base portion comprising a bottom wall extending from the first sidewall portion of the first flange to the second sidewall portion of the second flange; and
   an indentation extending from the proximal end to the distal end along the major length of the strap, the indentation formed by the first sidewall portion, the second sidewall portion, and the base portion, wherein the first flange and the second flange include bottom portions that make contact with and compress a tissue layer to position the tissue layer towards the base portion within the indentation as the subcutaneous device further advances the tissue layer to be positioned against one or more of the first sidewall portion, the second sidewall portion and the base portion of the indentation during placement of the subcutaneous device; a tunneling tool having a tip to form a space between a first plane of tissue and a second plane of tissue as the tunneling tool is inserted into an incision in a patient's body; and a channel extending though the strap from the proximal end to the distal end along the major length of the strap; and wherein the strap is configured as a mechanical guide for guiding the placement of the tunneling tool as the tunneling tool is inserted along the indentation and into the space between the first plane of tissue and the second plane of tissue of the patient's body; and a vacuum system coupled to the strap for pulling the patient's skin upward to be positioned within the indentation.

12. A medical device system for advancing a subcutaneous device to a desired implant site, the system comprising:
   a strap having a major length extending from a proximal end to a distal end and comprising a material from the proximal end to the distal end of the strap, and that conforms to a patient's body when the strap is attached to the patient's body;
   a hollow channel extending through the material a tunneling tool, the strap configured as a mechanical guide for guiding the placement of the tunneling tool as the tunneling tool is inserted into the patient's body prior to inserting the tunneling tool into the patient's body;
   a first flange comprising a first sidewall portion and a second flange comprising a second sidewall portion, the first flange and the second flange extending along the major length of the strap from the proximal end to the distal end;
   a base portion extending along the major length of the strap from the proximal end to the distal end, the base portion comprising a bottom wall extending from the first sidewall portion of the first flange to the second sidewall portion of the second flange;
   an indentation extending from the proximal end to the distal end of the major length of the strap, the indentation formed by the first sidewall portion, the second sidewall portion, and the base portion, wherein the first flange and the second flange include bottom portions that make contact with and compress a tissue layer to position the tissue layer towards the base portion within the indentation as the subcutaneous device further advances the tissue layer to be positioned against one or more of the first sidewall portion, the second sidewall portion and the base portion of the indentation during placement of the subcutaneous device in a space created by the tunneling tool between a first plane of tissue and a second plane of tissue after the tunneling tool has been advanced into the patient's body through an incision and along the indentation of the strap; and means for attaching the bottom portions to a patient's skin that comprises an adhesive.

* * * * *